US008481316B2

(12) United States Patent
Schumacher et al.

(10) Patent No.: US 8,481,316 B2
(45) Date of Patent: Jul. 9, 2013

(54) METHOD FOR DIFFERENTIATING EMBRYONIC STEM CELLS INTO CELLS EXPRESSING AQP-1

(75) Inventors: Karl M. Schumacher, Singapore (SG); Jackie Y. Ying, Singapore (SG); Annegret Schumacher, Singapore (SG); Karthikeyan Narayanan, Singapore (SG); Gunter Maubach, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 289 days.

(21) Appl. No.: 12/669,457

(22) PCT Filed: Jul. 21, 2008

(86) PCT No.: PCT/SG2008/000263
§ 371 (c)(1),
(2), (4) Date: Nov. 29, 2010

(87) PCT Pub. No.: WO2009/011663
PCT Pub. Date: Jan. 22, 2009

(65) Prior Publication Data
US 2011/0070280 A1 Mar. 24, 2011

Related U.S. Application Data

(60) Provisional application No. 60/929,960, filed on Jul. 19, 2007.

(51) Int. Cl.
*C12N 5/00* (2006.01)
*C12N 5/02* (2006.01)
*C12N 5/071* (2010.01)

(52) U.S. Cl.
USPC ............................ 435/377; 435/366; 435/384

(58) Field of Classification Search
USPC .......................................... 435/377, 366, 384
See application file for complete search history.

(56) References Cited

U.S. PATENT DOCUMENTS

| 7,229,827 B2 | 6/2007 | Kim et al. |
| 7,294,510 B2 | 11/2007 | Okano et al. |
| 7,326,572 B2 | 2/2008 | Fisk et al. |
| 2007/0031966 A1 | 2/2007 | Dressler et al. |
| 2008/0108044 A1 | 5/2008 | Rajesh et al. |

FOREIGN PATENT DOCUMENTS

| WO | 02078449 A2 | 10/2002 |
| WO | 2005021738 A1 | 3/2005 |

OTHER PUBLICATIONS

Jenq et al., Biochem. & Biophys. Res. Communication 256(1): 240-248, 1999.*
Hoffman et al. Nature Biotech., 23(6): 699-708, 2005.*
Lonza website, Renal Cell Growth Medium, pp. 1-2, accessed online at www.lonza.com on Sep. 18, 2012.*
Schumacher et al., In Vitro Cell. Dev. Biol., 35: 465-471, 1999.*
Liu et al., Reproductive Biology and Endocrinology 3(18): 1-10, 2005.*
Dantzler, W.H., "Regulation of renal proximal and distal tubule transport: Sodium, chloride and organic anions.", Comparative Biochemistry and Physiology Part A: Molecular & Integrative Physiology, Nov. 2003, pp. 453-478, vol. 136, Issue 3.
Kriz, W. et al., "Stability and leakiness: Opposing challenges to the glomerulus.", Kidney International, Jun. 1996, pp. 1570-1574, vol. 49, Issue 6.
Murer, H. et al., "Proximal tubular phosphate reabsorption: Molecular mechanisms.", Physiological Reviews, Oct. 1, 2000, pp. 1373-1409, vol. 60, Issue 4.
Katsura, T. et al., "Constitutive and regulated membrane expression of aquaporin 1 and aquaporin 2 water channels in stably transfected LLC-PK1 epithelial cells.", Proceedings of the National Academy of Sciences of the United States of America, Aug. 1, 1995, pp. 7212-7216, vol. 92, Issue 16.
Nielsen, S. et al., "Regulation and dysregulation of aquaporins in water balance disorders.", Journal of Internal Medicine, Jan. 2007, pp. 53-64, vol. 261, Issue 1.
Verkman, A.S., "Roles of aquaporins in kidney revealed by transgenic mice.", Seminars in Nephrology, May 2006, pp. 200-208, vol. 26, No. 3.
Humes, H.D. et al., "Initial clinical results of the bioartificial kidney containing human cells in ICU patients with acute renal failure.", Kidney International, Oct. 2004, pp. 1578-1588, vol. 66, Issue 4.
Saito, A. et al., "Present status and perspectives of bioartificial kidneys.", Journal of Artificial Organs, Sep. 2006, pp. 130-135, vol. 9, No. 3.
Tiranathanagul, K. et al., "Bioartificial kidney in the treatment of acute renal failure associated with sepsis.", Nephrology, Aug. 2006, pp. 285-291, vol. 11, Issue 4.
Atala, A. and Koh, C.J., "Tissue engineering applications of therapeutic cloning.", Annual Review of Biomedical Engineering, Aug. 2004, pp. 27-40, vol. 6.
Kim, D. and Dressler, G.R., "Nephrogenic factors promote differentiation of mouse embryonic stem cells into renal epithelia", Journal of the American Society of Nephrology, Dec. 1, 2005, pp. 3527-3534, vol. 16, Issue 12.
Little, M.H., "Regrow or repair: Potential regenerative therapies for the kidney.", Journal of the American Society of Nephrology, Sep. 1, 2006, pp. 2390-2401, vol. 17, Issue 9.
Steenhard, B.M. et al., "Integration of embryonic stem cells in metanephric kidney organ culture.", Journal of the American Society of Nephrology, Jun. 1, 2005, pp. 1623-1631, vol. 16, Issue 6.
Yamamoto, M. et al., "Branching ducts similar to mesonephric ducts or ureteric buds in teratomas originating from mouse embryonic stem cells.", American Journal of Renal Physiology: Renal Physiology, Jan. 1, 2006, pp. F52-F60, vol. 29, Issue 1.
Thomson, J.A. et al., "Embryonic stem cell lines derived from human blastocysts.", Science, Nov. 6, 1998, pp. 1145-1147, vol. 282, No. 5391.
Richards, M. et al., "Human feeders support prolonged undifferentiated growth of human inner cell masses and embryonic stem cells.", Nature Biotechnology, Sep. 2002, pp. 933-936, vol. 20, Issue 9.
Wang, G. et al., "Noggin and bFGF cooperate to maintain the pluripotency of human embryonic stem cells in the absence of feeder layers.", Biochemical and Biophysical Research Communications, May 13, 2005, pp. 934-942, vol. 330, Issue 3.

(Continued)

Primary Examiner — Thaian N Ton
(74) Attorney, Agent, or Firm — Klarquist Sparkman, LLP

(57) ABSTRACT

The present invention relates to methods of differentiating a human embryonic stem (ES) cell into a cell, specifically a renal epithelial cell, expressing AQP-I. The methods disclosed comprise culturing human ES cells in a renal specific medium in the presence of an extracellular matrix molecule. The cells produced according to said method can be used to treat renal related disorders such as renal failure, nephrosis, Bright's disease and glomerulitis.

6 Claims, 8 Drawing Sheets

OTHER PUBLICATIONS

Xu, C. et al., "Feeder-free growth of undifferentiated human embryonic stem cells.", Nature Biotechnology, Oct. 2001, pp. 971-974, vol. 19, Issue 10.

Baer, P.C. et al., "Differentiation status of human renal proximal and distal tubular epithelial cells in vitro: Differential expression of characteristic markers.", Cells Tissues Organs, Dec. 2006, pp. 16-22, vol. 184, No. 1.

Davies, J.A., "Morphogenesis of the metanephric kidney.", Scientific World Journal, Jun. 28, 2002, pp. 1937-1950, vol. 2.

James, R.G. and Schultheiss, T.M., "BMP signaling promotes intermediate mesoderm gene expression in a dose-dependent, cell-autonomous and translation-dependent manner.", Developmental Biology, Dec. 1, 2005, pp. 113-125, vol. 288, Issue 1.

Pal, R. and Khanna, A., "Similar pattern in cardiac differentiation of human embryonic stem cell lines, BG01V and ReliCellhES1, under low serum concentration supplemented with bone morphogenetic protein-2.", Differentiation, Feb. 2007, pp. 112-122, vol. 75, Issue 2.

Baeuerle, P.A. and Gires, O., "EpCAM (CD326) finding its role in cancer.", British Journal of Cancer, Feb. 2007, pp. 417-423, vol. 96, Issue 3.

Bussolati, B. et al., "Isolation of Renal Progenitor Cells from Adult Human Kidney", American Journal of Pathology, Feb. 2005, pp. 545-555, vol. 166, Issue 2.

Sagrinati, C. et al., "Isolation and Characterization of Multipotent Progenitor Cells from the Bowman's Capsule of Adult Human Kidneys", Journal of the American Society of Nephrology, Sep. 1, 2006, pp. 2443-2456, vol. 17, Issue 9.

Maness, P.F. and Schachner, M., "Neural recognition molecules of the immunoglobulin superfamily: signaling transducers of axon guidance and neuronal migration", Nature Neuroscience, Jan. 2007, pp. 19-26, vol. 10, Issue 1.

Schumacher, K. et al., "Perfusion Culture Improves the Maintenance of Cultured Liver Tissue Slices", Tissue Engineering, Jan. 13, 2007, pp. 197-205, vol. 13, Issue 1.

Itskovitz-Eldor, J. et al., "Differentiation of Human Embryonic Stem Cells into Embryoid Bodies Comprising the Three Embryonic Germ Layers", Molecular Medicine, Feb. 2000, pp. 88-95, vol. 6, Issue 2.

Bruce, S.J. et al., "In vitro differentiation of murine embryonic stem cells toward a renal lineage", Differentiation, Jun. 2007, pp. 337-349, vol. 75, Issue 5.

Reubinoff, B.E. et al., "Embryonic stem cell lines from human blastocysts: somatic differentiation in vitro", Nature Biotechnology, Apr. 2000, pp. 399-404, vol. 18, Issue 4.

Kouskoff, V. et al., "Sequential development of hematopoietic and cardiac mesoderm during embryonic stem cell differentiation", Proceedings of the National Academy of Sciences of the United States of America, Sep. 13, 2005, pp. 13170-13175, vol. 102, Issue 37.

Schuldiner, M. et al., "Effects of eight growth factors on the differentiation of cells derived from human embryonic stem cells", Proceedings of the National Academy of Sciences of the United States of America, Oct. 10, 2000, pp. 11307-11312, vol. 97, Issue 21.

Singla, D.K. and Sobel, B.E., "Enhancement by growth factors of cardiac myocyte differentiation from embryonic stem cells: A promising foundation for cardiac regeneration", Biochemical and Biophysical Research Communications, Sep. 30, 2005, pp. 637-642, vol. 335, Issue 3.

Karp, J.M. et al., "Cultivation of human embryonic stem cells without the embryoid body step enhances osteogenesis in vitro", Stem Cells, Apr. 2006, pp. 835-843, vol. 24, Issue 4.

Mukhina, S. et al., "Autocrine Growth Hormone Prevents Lactogenic Differentiation of Mouse Mammary Epithelial Cells", Endocrinology, Apr. 1, 2006, pp. 1819-1829, vol. 147, Issue 4.

Pera, M.F., "Human pluripotent stem cells: a progress report", Current Opinion in Genetics & Development, Oct. 1, 2001, pp. 595-599, vol. 11, Issue 5.

Baud, L., "Renal Epithelial Cells: Differentiation and Plasticity", Journal of the American Society of Nephrology, Jun. 1, 2003, pp. S1-S2, vol. 14, Supplement 1.

Kramer J. et al., "Cells differentiated from mouse embryonic stem cells via embryoid bodies express renal marker molecules", Differentiation, Mar. 2006, pp. 91-104, vol. 74, Issues 2-3.

Kobayashi, T. et al., "Wnt4-transformed mouse embryonic stem cells differentiate into renal tubular cells", Biochemical and Biophysical Research Communications, Oct. 21, 2005, pp. 585-595, vol. 336, Issue 2.

International Search Report & Written Opinion (issued in PCT/SG2008/000263), dated Oct. 23, 2008.

International Preliminary Report on Patentability (issued in PCT/SG2008/000263), dated Jan. 19, 2010.

Extended European Search Report and Opinion (issued in EP Application No. 08779492) dated Jul. 20, 2010.

First Examination Report dated Jun. 7, 2011 (issued in EP Application No. 08779492.1).

1st Office Action issued in Chinese Patent Application No. 200880107638.8 (with English translation) date of Issue—Jun. 9, 2011.

2nd Office Action dated Dec. 31, 2011 (issued in corresponding Chinese Patent Application No. 200880107638.8).

English Translation of 2nd Office Action dated Dec. 31, 2011 (issued in corresponding Chinese Patent Application No. 200880107638.8).

2nd Examination Report dated Feb. 28, 2013 (issued in European Patent Application No. 08779492.1).

Chung, Y. et al. "Human Embryonic Stem Cell Lines Generated without Embryo Destruction," Cell Stem Cell 2, Feb. 2008, pp. 113-117.

1st Examination Report dated Apr. 15, 2013 issued in corresponding Japanese Patent Application 2010-516953.

* cited by examiner

SEQUENCE LISTING

<160> NUMBER OF SEQ ID NOS: 18

<210> SEQ ID NO 1
<211> LENGTH: 17
<212> TYPE: DNA
<213> ORGANISM: artificial

-continued

```
<220> FEATURE:
<223> OTHER INFORMATION: synthetic primer

<400> SEQUENCE: 1
cccatgcacc gctacga                                                        17

<210> SEQ ID NO 2
<211> LENGTH: 18
<212> TYPE: DNA
<213> ORGANISM: artificial
<220> FEATURE:
<223> OTHER INFORMATION: synthetic primer

<400> SEQUENCE: 2
ggtgccctgc tgcgagta                                                       18

<210> SEQ ID NO 3
<211> LENGTH: 23
<212> TYPE: DNA
<213> ORGANISM: artificial
<220> FEATURE:
<223> OTHER INFORMATION: synthetic primer

<400> SEQUENCE: 3
tcctccatgg atctgcttat tca                                                 23

<210> SEQ ID NO 4
<211> LENGTH: 25
<212> TYPE: DNA
<213> ORGANISM: artificial
<220> FEATURE:
<223> OTHER INFORMATION: synthetic primer

<400> SEQUENCE: 4
cttccttttt tgcgacacta ttctc                                               25

<210> SEQ ID NO 5
<211> LENGTH: 19
<212> TYPE: DNA
<213> ORGANISM: artificial
<220> FEATURE:
<223> OTHER INFORMATION: synthetic primer

<400> SEQUENCE: 5
agtgcccgaa acccacact                                                      19

<210> SEQ ID NO 6
<211> LENGTH: 18
<212> TYPE: DNA
<213> ORGANISM: artificial
<220> FEATURE:
<223> OTHER INFORMATION: synthetic primer

<400> SEQUENCE: 6
ttctggcgcc ggttacag                                                       18

<210> SEQ ID NO 7
<211> LENGTH: 17
<212> TYPE: DNA
<213> ORGANISM: artificial
<220> FEATURE:
<223> OTHER INFORMATION: synthetic primer

<400> SEQUENCE: 7
cgttcggccc aggctaa                                                        17
```

```
<210> SEQ ID NO 8
<211> LENGTH: 25
<212> TYPE: DNA
<213> ORGANISM: artificial
<220> FEATURE:
<223> OTHER INFORMATION: synthetic primer

<400> SEQUENCE: 8
caagccagaa gatgaagtta aatcc                                          25

<210> SEQ ID NO 9
<211> LENGTH: 20
<212> TYPE: DNA
<213> ORGANISM: artificial
<220> FEATURE:
<223> OTHER INFORMATION: synthetic primer

<400> SEQUENCE: 9
cggaggttcg aagacgatca                                                20

<210> SEQ ID NO 10
<211> LENGTH: 19
<212> TYPE: DNA
<213> ORGANISM: artificial
<220> FEATURE:
<223> OTHER INFORMATION: synthetic primer

<400> SEQUENCE: 10
ggcgggtcat gggaataac                                                 19

<210> SEQ ID NO 11
<211> LENGTH: 20
<212> TYPE: DNA
<213> ORGANISM: artificial
<220> FEATURE:
<223> OTHER INFORMATION: synthetic primer

<400> SEQUENCE: 11
ccacctcctt gggatccatt                                                20

<210> SEQ ID NO 12
<211> LENGTH: 19
<212> TYPE: DNA
<213> ORGANISM: artificial
<220> FEATURE:
<223> OTHER INFORMATION: synthetic primer

<400> SEQUENCE: 12
gtgacgacag ctggagcca                                                 19

<210> SEQ ID NO 13
<211> LENGTH: 18
<212> TYPE: DNA
<213> ORGANISM: artificial
<220> FEATURE:
<223> OTHER INFORMATION: synthetic primer

<400> SEQUENCE: 13
cccatcgtgt ccccactc                                                  18

<210> SEQ ID NO 14
<211> LENGTH: 20
<212> TYPE: DNA
<213> ORGANISM: artificial
<220> FEATURE:
<223> OTHER INFORMATION: synthetic primer

<400> SEQUENCE: 14
```

-continued

```
gccgatcatc agctggtaca                                           20

<210> SEQ ID NO 15
<211> LENGTH: 21
<212> TYPE: DNA
<213> ORGANISM: artificial
<220> FEATURE:
<223> OTHER INFORMATION: synthetic primer

<400> SEQUENCE: 15
acatggaggt ggaggacaac a                                         21

<210> SEQ ID NO 16
<211> LENGTH: 19
<212> TYPE: DNA
<213> ORGANISM: artificial
<220> FEATURE:
<223> OTHER INFORMATION: synthetic primer

<400> SEQUENCE: 16
cccggtcaac gtcaatcac                                            19

<210> SEQ ID NO 17
<211> LENGTH: 20
<212> TYPE: DNA
<213> ORGANISM: artificial
<220> FEATURE:
<223> OTHER INFORMATION: synthetic primer

<400> SEQUENCE: 17
ggcctcagtg ttgtgtatta                                           20

<210> SEQ ID NO 18
<211> LENGTH: 18
<212> TYPE: DNA
<213> ORGANISM: artificial
<220> FEATURE:
<223> OTHER INFORMATION: synthetic primer

<400> SEQUENCE: 18
gagccaaggg ttcactac                                             18
```

METHOD FOR DIFFERENTIATING EMBRYONIC STEM CELLS INTO CELLS EXPRESSING AQP-1

CROSS-REFERENCE TO RELATED APPLICATION

This application claims benefit of, and priority from, U.S. provisional patent applications No. 60/929,960, filed on Jul. 19, 2007, the contents of which are fully incorporated herein by reference.

FIELD OF THE INVENTION

The present invention relates to methods for differentiating embryonic stem cells into cells expressing AQP-1.

BACKGROUND OF THE INVENTION

Various approaches in regenerative medicine that are aimed at replacing lost functions of organs are limited by a lack of sources of sufficient cells. Thus, significant research has been directed towards exploring human embryonic stem (hES) cells as a potential cell source. Human embryonic stem (hES) cells are capable of indefinite self-renewal and are pluripotent; that is, these cells are able to differentiate into practically every type of cell found in the organism from which they are derived (2,3). As such, hES cells may provide a supply of different cell types for use in a variety of research and medical purposes.

One such use is in the treatment of renal disease and loss of renal function. The increasing prevalence of type II diabetes has led to a growing incidence of end-stage renal disease. This increased prevalence combined with the limited alternatives for treatment has made kidney disease a major world-wide health problem (2,4).

The major functions of the kidney include the elimination of metabolic waste products and the regulation of water, electrolyte and acid-base balance. These are mainly achieved by (i) a filtration process that takes place in the glomeruli and leads to the formation of a primary filtrate volume of 180 l/day, and (ii) a reabsorption process in the subsequent tubular system (5-7). Upon filtration, most of the water and the dissolved substances return through transport over the proximal tubulus epithelium, back to the capillary system with or without reduced reabsorption of the metabolic waste products (5-7). The massive water reabsorption is enabled by a specific water-transporting channel protein named aquaporin-1 (AQP-1), which is localized on the cell membranes of epithelial cells, lining the renal proximal tubulus structures as a monolayer (8-10).

Artificial devices have been designed to mimic renal function. In such devices a size-selective filtration process normally performed by the glomeruli can be performed by polymer membranes that are assembled as hollow fibers in cartridges, and devices for hemodialysis or hemofiltration have been proven successful in clinical applications. In contrast, development of methods to mimic the renal reabsorption function seems to be highly dependent on the specific functionalities of renal cells (11-12).

SUMMARY OF THE INVENTION

The present invention provides a method for generating from human embryonic stem (hES) cells in vitro cells that can transport water in a manner similar to renal epithelial cells. The method involves culturing the hES cells in renal-specific growth medium and in the presence of an extracellular matrix molecule to provide nephrogenic differentiation conditions that induce differentiation into cells expressing aquaporin 1 (AQP-1).

Thus the present method has the potential to provide a much needed cell source for the therapy including the treatment of lost renal function through bioartificial devices, cell therapies to replace epithelial tissues and tissue engineering.

In one aspect, there is provided a method of differentiating a human embryonic stem (hES) cell into a cell expressing AQP-1, the method comprising culturing an undifferentiated hES cell in a renal-specific culture medium in the presence of an extracellular matrix (ECM) molecule, under conditions sufficient to induce differentiation of the hES cell to a cell expressing AQP-1.

In different embodiments, the renal-specific culture medium may comprise renal epithelial basal medium or renal epithelial growth medium and may comprise epithelial growth factor. The ECM molecule may comprise at least one of fibronectin, laminin, collagen IV and Matrigel matrix. Bone morphogenetic protein 2 may be added to the renal-specific culture medium before or during culturing of the cell.

In one embodiment, the method comprises adding bone morphogenetic protein 2 to the renal-specific culture medium at a concentration of from about 2.5 to about 10 ng/ml before or during culturing, wherein culturing comprises growing the cells for 7-10 days, the renal-specific culture medium comprises renal epithelial growth medium and the ECM molecule comprises Matrigel matrix, and wherein once differentiated, the cell expresses AQP-1 and at least one of CK-18, β-catenin, CD-326 and CD-133.

In another aspect, there is provided a population of cells differentiated directly from a population of human embryonic stem cells in a renal-specific culture medium and in the presence of an extracellular matrix molecule, wherein about 2% to about 50% of the cells express AQP-1. The population of cells may be prepared by the methods as described herein.

In yet another aspect, there is provided a bioartificial tubule assist device comprising a hollow core fibre having an interior lumen, the interior lumen coated with an extracellular matrix (ECM) molecule and a population of cells as described herein.

In a further aspect, there is provided a method of preparing a bioartificial tubule assist device, the method comprising providing a bioartificial tubule assist device comprising a hollow core fibre having an interior lumen and seeding the interior lumen with a population of cells as described herein, wherein the interior lumen is coated with an extracellular matrix molecule prior to seeding with the population of cells.

The extracellular matrix molecule may comprise at least one of fibronectin, laminin, collagen IV and Matrigel matrix. The cells may be cultured to a confluent monolayer coating the interior lumen.

In still a further aspect, there is provided a method of treating a renal related disorder in a subject in need thereof, the method comprising implanting an effective amount of a population of cells as described herein in the subject at a site where cells expressing AQP-1 are required. The cells may be implanted directly or may be provided in a bioartificial tubule assist device.

In yet a further aspect, there is provided a method of treating a renal related disorder in a subject comprising externally connecting a bioartificial tubule assist device as described herein to a subject in need thereof.

The renal related disorder may comprise renal failure, nephropathy, diabetic nephropathy, nephrosis, Bright's disease, renal insufficiency, glomerulitis, glomerulosclerosis or nephritis.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
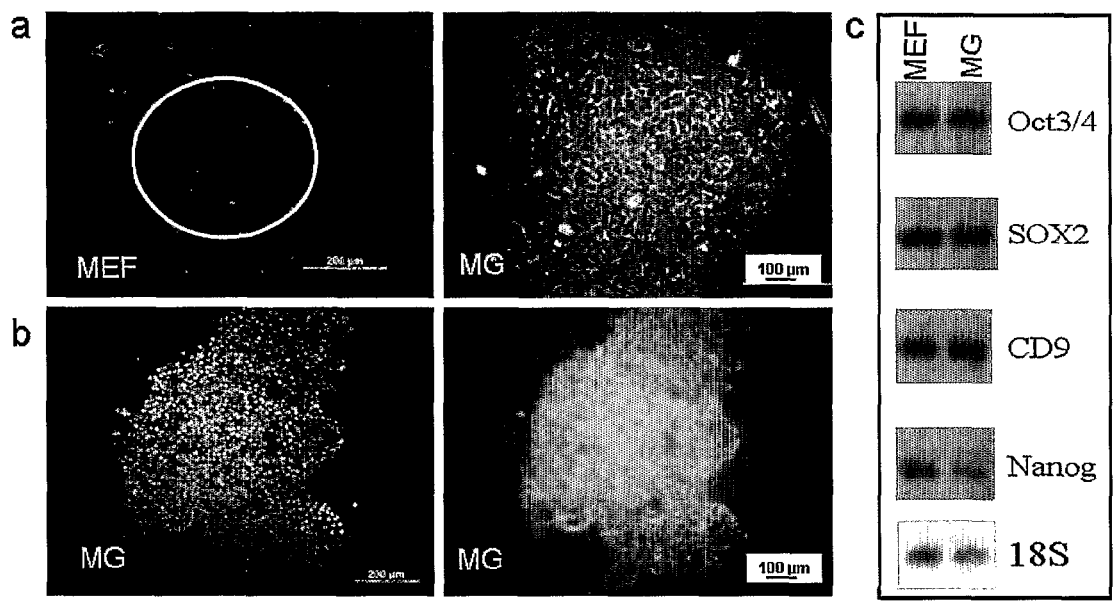
FIG. 1: Culture of Undifferentiated hES Cells. a, hES cells cultured on a MEF feeder layer, and on MATRIGEL™ (MG) with MEF-derived conditioned medium. b, Immunostaining of hES cells showed expression of Oct3/4 (red). DAPI was used to stain the nucleus (blue). c, Gene expression analysis by RT-PCR for stem cell specific markers such as Oct3/4, Sox2, CD9 and Nanog in the two culture conditions.

In vitro differentiation of hES cells into hematopoietic, neuronal and cardiac cells has been observed (1,13,14) and studies have shown that different culture conditions, including the presence of different growth factors, favour the formation and growth of particular cell types (13,15,16). However there has been no report of directed in vitro differentiation of hES cells into human renal epithelial cells.

Recently, studies have reported successful directed differentiation of mouse embryonic stem (mES) into renal progenitor cells (4,17). The addition of factors including activin A, retinoic acid, bone morphogenetic protein (BMP) 7 and BMP4 to culture media has been shown to induce differentiation into renal progenitor cells. However, the methods disclosed in these studies are limited to the differentiation of mES cells and are not instructive on the differentiation of hES cells. Differences exist between the differentiation of mES and hES cells and the effect of cellular factors and signals on these cells. For example, when cells are grown on tissue culture dishes in vitro, the presence of leukemia inhibitory factor (LIF) causes mES cells to remain in an undifferentiated state while hES cells lose pluripotency and differentiate rapidly despite the presence of LIF (3,18). Similarly, BMP4 suppresses differentiation of mES cells but promotes differentiation of hES cells (3). mES and hES cells also differ in the stages of differentiation when certain cell surface markers are present, suggesting basic species differences between the differentiation of ES cells in early mouse and early human development (19).

The reported methods of inducing differentiation of mES to a renal lineage have employed indirect differentiation through embryoid body (EB) formation. However, such an approach results in a heterogeneous population of differentiated cells and a low yield of renal progenitor cells.

To date, there has been no published report of aquaporin 1 (AQP-1) positive epithelial cells derived from hES cells using a direct differentiation protocol. As stated above, AQP-1 is a water-transporting channel protein localized on the cell membranes of renal epithelial cells that line the renal proximal tubulus structures. AQP-1 plays a role in the water reabsorption function of the kidneys.

The present methods are based on the finding that human embryonic stem (hES) cells can be induced in vitro to differentiate into renal epithelial-like cells possessing water transport functionality by culturing them in renal-specific culture conditions. The present methods provide a method to differentiate hES cells to cells expressing AQP-1. The differentiated hES cells produced by the present methods could be cultured for a period of 7 days in a perfusion bioreactor without loss in the AQP-1 expression. The methods include culturing hES cells in a renal-specific culture medium in the presence of an extracellular matrix (ECM) molecule to provide nephrogenic differentiation conditions. The cells produced by the present methods may also exhibit a similar CD receptor expression profile as that found in human proximal tubule cells. Thus, the present methods provide a differentiation protocol for the generation of functional renal epithelial-like cells.

When used to differentiate a population of cells, the present methods result in from about 2% or more, and in some instances from about 2% to about 50% of the cells in the population differentiating to renal epithelial-like cells expressing AQP-1. Thus, when used to differentiate a population of cells, the methods described herein may result in some but not all of the hES cells differentiating to renal epithelial-like cells.

When added to a renal-specific culture medium, epithelial growth factor (EGF) and/or bone morphogenetic protein-2 (BMP-2) were found to increase differentiation of hES cells to renal epithelial-like cells as compared to the use of a renal-specific culture medium without one or both of these or factors. As well, multiple passages or sub-culturing of a population of cells may increase the proportion of cells that differentiate into renal epithelial-like cells possessing water transport functionality.

The present method allows for the direct differentiation of hES cells into renal epithelial-like cells without the formation of embryoid bodies (EBs). An EB is an aggregate of cells that can facilitate differentiation comparable to an embryo and thus can contains cells from all three germ layers, the ectoderm, meosderm and endoderm. In indirect differentiation, ES cells are first aggregated to form EBs and then the EBs are exposed to conditions to promote differentiation into renal progenitor cells. Since the formation of EBs leads to the formation of multiple cell types, indirect differentiation using EBs results in a heterogeneous population of differentiated cells and a low yield of renal progenitor cells. Omission of the formation of embryoid bodies in a hES cell differentiation protocol was found improve the efficiency of differentiation into osteogenic cells (20). Thus, without being limited to any particular theory, it appears that the present method allows for a relatively uniform cellular environment and a more homogeneous population of differentiated cells, and thus is likely to provide a higher yield of renal epithelial-like cells than methods involving the formation of EBs.

As used herein, the term "renal epithelial-like cell" refers to a cell or cells that are differentiated directly from hES cells to express renal epithelial cell protein markers, including one or more of CK-18, β-catenin, AQP-1, AQP-2, AQP-4 and megalin. A renal epithelial cell protein marker includes a cellular protein expressed in human renal epithelial cells and which is not expressed or is expressed to a lesser extent in human embryonic stem cells. Such a marker may be used as indication that a particular cell has differentiated from an hES cell to become a renal epithelial-like cell.

"Water transporting functionality" refers to a characteristic of a cell, or a cell population that includes cells, expressing AQP-1 and is thus able to take up water in a manner functionally similar to a renal epithelial cell involved in water reabsorption. Thus, a cell that possesses water transporting functionality expresses AQP-1 and is able to, has the capability of, or can function to take up water as in the renal reabsorption process.

Thus, there is provided a method of differentiating human embryonic stem cells into cells expressing AQP-1. The method comprises culturing hES cells in a renal-specific culture medium in the presence of an extracellular matrix (ECM) molecule.

The hES cells used in the present method are undifferentiated hES cells.

As used herein, the term "cell" when referring to a human embryonic stem cell is intended to refer to a single cell as well as a plurality or population of cells. Similarly, the term "cells" is also intended to refer to a single cell, where context allows. The cell may be a cell grown in batch culture or in tissue culture plates. The undifferentiated hES cell or cells are typically originally obtained from a blastocyst, as is known in the art, but may be previously expanded while kept in an undifferentiated state.

Generally, methods of culturing hES cells to maintain the cells in an undifferentiated state is known and thus the hES cells may be maintained in an undifferentiated state using known methods for hES cells, with or without feeder cells, prior to use in the present method. In one embodiment, undifferentiated hES cells are maintained by culturing the hES cells on a feeder cell layer, such as mouse embryonic fibroblast (MEF) feeder layer. In another embodiment, the hES cells used in the methods may be from a feeder-free culture. For example, hES cells first cultured with feeder cells, such as MEFs, may then be cultured in the absence of feeder cells on extracellular matrix molecule, including for example MATRIGEL™. In one embodiment, the hES cells used are first cultured on a layer of MEFs and then subsequently cultured on a MATRIGEL™ layer using condition medium collected from the MEF feeder layer in order to obtain fibroblast-free undifferentiated hES cells.

In order to induce differentiation, the undifferentiated hES cells are cultured in a renal-specific culture medium. The renal-specific culture medium may be any growth medium designed to support the growth of renal cells and that contains nutrients and factors required to maintain attachment, growth and proliferation of hES and induce the hES cells to differentiate and express AQP-1. The renal-specific growth medium may contain basal factors to allow for expansion of a renal cell population, and may also be supplemented with additional factors, including fetal calf serum (FCS), growth factors such as epidermal growth factor (EGF) and basic fibroblast growth factor (bFGF), insulin, hydrocortisone, epinephrine, and tri-iodothyronine (T3). Renal-specific culture media are known and may be commercially available, including renal epithelial basal medium (REBM) and renal epithelial growth medium (REGM, available from Cambrex, USA).

The renal-specific culture medium may be supplemented with EGF, for example about 0.05% to about 2.0% EGF, about 0.05% to about 1.0% EGF, about 0.075% to about 0.5% EGF, or about 0.1% to about 0.25%. The renal-specific culture medium may also be supplemented with BMP-2, for example about 0.5 to about 50 ng/ml BMP-2, about 1 to about 25 ng/ml BMP-2, or about 2.5 to about 10 ng/ml BMP-2.

In one embodiment, REGM is used as the renal-specific growth medium. REGM comprises REBM supplemented with about 0.25% FCS, about 0.1% EGF, about 0.1% insulin, about 0.1% hydrocortisone, about 0.1% epinephrine, and about 0.1% tri-iodothyronine.

Without being limited to any particular theory, based on observations of the effect of omitting different factors from REGM, FCS may be required for hES cell attachment. In addition, insulin, epinephrine and transferrin may play roles in hES cell proliferation and EGF may play a role in inducing differentiation of the hES cells to renal epithelial-like cells. Thus, the renal-specific culture medium in one embodiment comprises FCS, insulin, epinephrine, transferrin and EGF. In another embodiment the renal-specific culture medium comprises EGF.

In addition to the renal-specific culture medium, an extracellular matrix (ECM) molecule is included in the growth conditions in order to induce the undifferentiated hES cells to differentiate into cells expressing AQP-1. In one embodiment, the hES cells are seeded on culture surface coated with ECM molecules to mimic the epithelial basement membrane. The ECM molecule may be any ECM molecule or mixture of ECM molecules that supports the growth of hES cells in renal-specific culture medium. For example, the ECM molecule may be fibronectin, laminin, collagen type IV or MATRIGEL™ (BD Biosciences). MATRIGEL™ Matrix is a solubulized basement membrane preparation extracted from EHS mouse sarcoma and comprises various basement membrane components and bound growth factors that are known to promote the establishment of epithelial tissues (22), including laminin, collagen IV, heparan sulfate proteoglycans and entactin.

The hES cells are grown in the renal-specific culture medium in the presence of the ECM molecule for a time period and at a temperature and under growth conditions sufficient to induce differentiation of at least some of the hES cells including expression of AQP-1.

For example, the cells may be cultured up to 30 days, for example from 5-15 days or from 7-10 days at 37° C. with 2-10% $CO_2$, or 5% $CO_2$.

As stated above, when the present methods are performed on a cell population such as a cell culture, not every cell within the population or culture will necessarily differentiate to a cell expressing AQP-1. Thus, some cells within the population or culture may not differentiate and may retain their hES nature while other cells within the same population or culture are induced to, differentiate and to express AQP-1.

Thus, the present method may result in differentiation of the hES cells to cells expressing AQP-1 to the extent that about 2% or more of the cells in the culture population express renal epithelial markers, including at least AQP-1 and which may also express one or more of CK-18, β-catenin, AQP-2, AQP-4 and megalin. For example, about 2% or more, about 5% or more, about 10% or more, about 15% or more, about 20% or more or about 25% or more of the cell population may express renal epithelial cell markers. In other embodiments, from about 2% to about 50%, from about 5% to about 50%, from about 10% to about 50%, from about 15% to about 50%, from about 20% to about 50%, or from about 25% to about 50% of the cells may differentiate cells expressing AQP-1 and possibly other renal epithelial markers.

The extent of differentiation to cells expressing AQP-1 may be readily determined by a skilled person using standard methodology, including as described in the Example below, such as immunohistochemical techniques, Western blot techniques and PCR techniques to confirm expression of particular marker proteins. Furthermore, similarity between the differentiated cell population produced by the method of the present invention and primary human proximal tubule cells may be demonstrated by CD receptor expression profile, including CD-326 and CD-133. In addition, the ability of the cells to transport water may be determined using methods as described in the Example below, including assaying for fluorescence before and after exposure to a hypotonic solution, using a fluorescent marker such as calcein.

Subculturing of the hES cells for one or more additional growth period in a renal-specific growth medium on an ECM molecule may increase the extent of differentiation of the hES cells to renal epithelial-like cells. For example, the cells may be removed from the initial culture medium, optionally washed and then placed in fresh renal-specific growth medium along with ECM molecule for an additional culture period, such as from 5-30 days, from 5-15 days or from 7-10 days. The cells may be passaged or subcultured multiple times, for example one, two, three, four times, which may increase the number of cells in the culture that have differentiated to express AQP-1.

Bone morphogenetic protein 2 (BMP-2) may be involved in switching on AQP-1 expression levels in single cells. Thus, BMP-2 may optionally be added to the culture medium to increase the number of AQP-1 positive cells obtained. For example, from about 1.0 to about 20 ng/ml or from about 2.5 to about 10 ng/ml BMP-2 may be included in the culture medium. The BMP-2 may be added to the culture medium at the beginning of the differentiation method, for example prior to adding cells to the culture medium, or the BMP-2 may be added at later stages in the differentiation method, including at any point at which the cells may be sub-cultured.

The present method conveniently provides in vitro generation of cells expressing AQP-1 from hES cells by directed differentiation. The generated cells can be used in cell therapies, including to treat lost renal function. In particular, the cells expressing AQP-1 of the present invention demonstrate water transport functionality which is essential to the water adsorption function of kidney epithelial cells. In addition, the renal epithelial-like cells of the present invention may be capable of maintaining a high degree of water-transporting channel protein aquaporin-1 (AQP-1) expression after 7 days of culture in a perfusion bioreactor, indicating utility in a BTAD. As will be understood, a perfusion culture model mimics an epithelial barrier by having a basal and luminal side.

Thus, the present method may be used to produce a cell expressing AQP-1 or a population of cells expressing AQP-1. As described above, the cell or population of cells may express other epithelial markers, including CK-18, β-catenin, CD-326 and CD-133. For a population of cells, about 2% or more, about 5% or more, about 10% or more, about 15% or more, about 20% or more or about 25% or more of the cell population may express AQP-1 and other renal epithelial cell markers. In other embodiments, from about 2% to about 50%, from about 5% to about 50%, from about 10% to about 50%, from about 15% to about 50%, from about 20% to about 50%, or from about 25% to about 50% of the cells may differentiate to express AQP-1 and other renal epithelial markers.

The presently described cells may be used in vivo or in vitro to provide cells possessing water transporting functionality and may be useful in regenerative strategies such as regenerative therapy and bioengineering. Regenerative therapy involves the use of cells to repair or replace diseased tissue or organs. For example, renal-like cells are delivered to a diseased kidney where they are incorporated to replace the function of damaged tissue (2). Bioengineering is another regenerative strategy that involves the use of organ specific cells in combination with other factors and a matrix to create a de novo replacement organ (2).

It has been previously recognized that embryonic stem cells could potentially provide a cell source for cell therapy strategies (17,23-25). However, prior to the present methods, directed in vitro generation of renal-like cells from hES cells was not known and the functionality of cells derived from hES in cell therapy strategies has been primarily hypothetical (2,12,26). As such, treatment of renal disease has been mainly focused on organ transplantation or gene therapy (26).

Previous studies have shown that the renal reabsorption function can be successfully conducted by human proximal tubule epithelial cells isolated from kidney donor organs and seeded on polysulfone hollow fiber systems (11). This approach has been successfully demonstrated in Phase I/II clinical trials, with an immunoprotective barrier on the polysulfone membrane to permit the use of allogeneic cell sources in a cell therapeutic application (11, 23). However, this approach is limited by the shortage of kidney donor organs. Organs will generally be transplanted if available, thus only in a few cases will the donor organs be used as a cell source for a bioartificial tubule assist device.

Due to their water transporting functionality, the cells expressing AQP-1 produced according to the present methods provide a readily obtainable source of cells that may be used in bioartificial tubule assist devices in strategies to replace lost renal function. Thus, also contemplated herein are devices and methods for the treatment of lost renal function that incorporate the differentiated cells expressing AQP-1 of the present invention.

The present invention provides a bioartificial tubule assist device containing cells expressing AQP-1 generated in vitro from hES cells, which device may be used for the treatment of lost kidney function.

Generally, bioartificial tubule assist devices are designed as hollow core fibres having an interior lumen. Typically, the lumen is formed at least in part by a tubular or flat bed having a porous surface or membrane. Cells are seeded on the porous surface or membrane and allowed to attach and expand in population on the surface. The surfaces are typically exposed to fluid on two sides (the cell free side and the side with seeded cells). Such devices are known in the art (Ingenta) and may be incorporated into bioreactor system or connected to a patient as in the manner of a dialysis device.

For example, in such a device a hollow-fiber hemofiltration cartridge with a membrane surface may be used as a scaffold for cell growth. The inner lumen of the hollow fiber may be coated with a suitable ECM molecule and cells added to the interior of the lumen in the presence of renal-specific culture medium as described above.

Thus, there is provided a method of preparing a device, the method comprising differentiating hES cells into cells expressing AQP-1 as described above, either before or after seeding the cells into an interior lumen of a hollow fibre device, the interior lumen coated with an ECM molecule, including one or more of fibronectin, laminin, collagen IV and Matrigel matrix.

The cell population may thus be grown on the inner surface of the hollow fiber to provide within the bioartificial tubule assist device a monolayer, including a confluent monolayer, of renal epithelial-like cells or a population in which some of the cells are differentiated to express AQP-1 as described above.

hES cells prior to differentiation may be seeded into the device and differentiated after seeding. Alternatively, the cells may be differentiated in a renal-specific culture medium prior to seeding into the device.

As stated above, the cells, once seeded into the interior of the hollow fiber device, may be expanded, including to confluence. Expansion may be performed by growing the cells under suitable conditions for growth and multiplication of the cell population using a renal-specific culture medium, as described above.

By placing the presently described cells within such a device, the cells may be used in clinical applications while being separated by blood circulation via artificial immunological barriers, reducing risk of immune rejection or other immune complications and risk of possible tumourigenesis which may occur with undifferentiated stem cells.

The above described bioartificial tubule assist device may be used to treat a subject having a renal related disorder. The cells within the bioartificial tubule assist device may act to reabsorb substances within the kidney ultrafiltrate, thus mimicking the filtration and reabsorption functions of a healthy kidney.

Thus, there is also presently provided a method of treating a renal related disorder in a subject. The method comprises connecting a bioartificial tubule assist device of the present invention to a subject in need thereof.

Treating a renal related disorder refers to an approach for obtaining beneficial or desired results, including clinical results. Beneficial or desired clinical results can include, but are not limited to, alleviation or amelioration of one or more symptoms or conditions, diminishment of extent of disorder or disease, stabilization of the state of disease, prevention of development of disorder or disease, prevention of spread of disorder or disease, delay or slowing of disorder or disease progression, delay or slowing of disorder or disease onset, amelioration or palliation of the disorder or disease state, and remission (whether partial or total). "Treating" can also mean prolonging survival of a subject beyond that expected in the absence of treatment. "Treating" can also mean inhibiting the progression of disorder or disease, slowing the progression of disorder or disease temporarily, although more preferably, it involves halting the progression of the disorder or disease permanently.

The subject may be any subject having a renal related disorder or requiring treatment for a renal related disorder. A renal related disorder refers to any disease, disorder or condition which may cause, result in, or is associated with renal degeneration or renal failure, including nephropathy, diabetic nephropathy, nephrosis, Bright's disease, renal insufficiency, glomerulitis, glomerulosclerosis, or nephritis.

As stated above, such devices and uses of such devices are known in the art. Generally, the device is used in a manner similar to a conventional dialysis device or hemofiltration device. The device is connected externally to a subject and the subject's blood or fluid is pumped through the device, past the membrane with the cells seeded on the opposite side of the membrane and then eventually back into the subject. The cells are able to transport water as the blood or fluid from the subject is passed through the device.

There is also presently provided a method of treating a renal related disorder in a subject comprising implanting a cell or device of the present invention in a subject in need thereof.

Implantable devices are known, for example as described in U.S. Pat. Nos. 6,150,164 and 6,942,879.

The cell or device may be implanted using standard surgical or injection methods. The cell or device may be implanted at a suitable site in the subject to provide therapeutic treatment of the renal related disorder, for example a site where renal epithelial cells are required, including in the renal proximal tubulus structure.

An effective amount of cells expressing AQP-1, including cells within a bioartificial tubule assist device, possessing water transporting functionality is administered to the subject. The term "effective amount" as used herein means an amount effective, at dosages and for periods of time necessary to achieve the desired result, for example, to treat the renal related disorder.

The number of total number cells to be administered will vary, depending on several factors, including the severity and type of the renal related disorder, the mode of administration, and the age and health of the subject.

It will be appreciated that the cells expressing AQP-1 may be administered to treat a renal related disorder in combination with other treatments or therapies, including drug therapy, dialysis treatment and surgery.

The present methods, cell populations, devices and uses are further exemplified by way of the following non-limited examples.

EXAMPLES

Example 1

In this example, human embryonic stem (hES) were seeded on various culture surfaces with different extracellular matrix (ECM) components and cultured in a renal epithelial growth medium (REGM). This method was applied to differentiate hES into renal epithelial-like cells. After 10 days of culture in REGM, immunohistochemistry and Western blotting revealed expression of AQP-1 and CK-18 indicating an epithelial phenotype. Flow cytometry showed that the differentiated cells had a CD receptor expression profile similar to that found in human renal proximal tubule. In addition, the differentiated cells exhibited functional water transport and could be cultured for 7 days in a perfusion bioreactor without loss of AQP-1 expression. Thus, this method provides a differentiation protocol for the generation of functional renal epithelial-like cells that can potentially be used in strategies to replace lost renal function.

Materials and Methods hES Cell Culture and Differentiation: The HUES-7 cell line (obtained from Howard Hughes Medical Institute, USA) was cultured at 37° C. with 5% of $CO_2$ on neomycin-resistant primary mouse fibroblasts, strain FVB (Cat. No. PMEF-N, CHEMICON International, USA) in Knock-out DMEM (Invitrogen, USA, Cat. No. 10829018) supplemented with 20% of serum replacement (Invitrogen, Cat. No. 10828028), 1% of GlutaMax (Invitrogen, Cat. No. 35050061), 1% of a nonessential amino acid solution (Invitrogen, Cat. No. 11140-050), 1% of penicillin-streptomycin (Invitrogen, Cat. No. 15070-063), 0.004% of basic fibroblast growth factor (bFGF) (Invitrogen, Cat. No. 13526029), and 0.1% of 2-mercaptoethanol (Invitrogen, Cat. No. 21985023). The primary mouse fibroblasts were plated on a T75 flask coated with 0.1% of gelatin (Sigma, USA). The culture medium was changed every day and cultured between 7 and 10 days. The conditioned culture media from MEF's were collected and used with hES cells along with 10 ng/ml of bFGF. The hES cells cultured on the fibroblast layer were trypsinized (0.05% of trypsin, Invitrogen, USA), scraped, and filtered through a 100-μm mesh. The filtered cells were cultured on a MATRIGEL™ Matrix (BD Biosciences, Germany) coated (diluted 1:20 in Knock-out DMEM) culture flask containing conditioned culture media from MEF's. The hES cells were subcultured twice to obtain fibroblast-free culture conditions (3,18,21). The expression of Oct3/4 (FIG. 1b), Sox2, CD9 and Nanog, detected by RT-PCR analysis, (FIG. 1c) confirmed the undifferentiated status of the hES cells.

Upon expansion, the cells were seeded on various ECM molecule coatings and cultured using REGM (Cambrex, USA) for 7-10 days. The ECM coatings were prepared as follows; fibronectin (Invitrogen, Cat. No. 33016015), 50 μg/ml in phosphate-buffered saline (PBS), natural mouse laminin (Invitrogen, Cat. No. 33016015), 1.3 mg/ml 1:15 diluted in PBS and collagen IV (BD Biosciences, Cat.-No. 354233)), 1:9 diluted in 0.05 M HCl. The solutions were each exposed for 1 h to the surface of the cell culture flask and than removed. The culture medium was changed every other day. The subcultivation was performed by using 2 ml of trypsin solution (Cambrex, Cat.-No. cc-5012) for 1-2 min, followed by the addition of 2 ml of trypsin neutralization solution (Cambrex, Cat. No. cc-5002). The cells were centrifuged at 500×g for 5 min. The culture medium was changed every other day. Human proximal tubule cells were cultured on a fibronectin-coated culture flask in REGM (Cambrex, USA). For certain experiments, BCP-2 was added at increasing concentration from 2.5 to 10 ng/ml to the REGM.

RNA Isolation and Two-Step RT-PCR: The total RNA was isolated from the cells using the NucleoSpin RNA II isolation kit (Macherey-Nagel, Germany) according to the manufacturer's protocol. One microgram of total RNA was reverse transcribed into cDNA using the High-capacity cDNA archive kit (Applied Biosystems, USA). Briefly, 50 μl of total RNA was mixed with 2× master mix containing RT buffer, dNTP mixture, random hexamer and MultiscribeRT (5 U/μl). The reaction mixture was incubated in a thermal cycler (PTC-200, MJ Research, USA) for 10 min at 25° C., followed by 2 h at 37° C. 1 μl of each cDNA was used in the PCR reaction with the Platinum PCR Supermix (Invitrogen, USA). The reaction conditions were 95° C. for 3 min, 94° C. for 30 s, 55° C. for 1 min, 72° C. for 1 min, amplified for 45 cycles. The primers for PCR were designed using the Primer Express 3.0 software (Applied Biosystems, USA) and the respective human sequences from Genbank. The primers were as follows: SOX2 sense CCCATGCACCGCTACGA [SEQ ID NO.: 1], antisense GGTGCCCTGCTGCGAGTA [SEQ ID NO.: 2], Nanog sense TCCTCCATGGATCTGCTTATTCA [SEQ ID NO.: 3], antisense CTTCCTTTTTTGCGACACTATTCTC [SEQ ID NO.: 4], Oct3/4 sense AGTGCCCGAAACCCACACT [SEQ ID NO.: 5], antisense TTCTGGCGCCGGTTACAG [SEQ ID NO.: 6], CD9 sense CGTTCGGCCCAGGCTAA [SEQ ID NO.: 7], antisense CAAGCCAGAAGATGAAGTTAAATCC [SEQ ID NO.: 8], 18S sense CGGAGGTTCGAAGACGATCA [SEQ ID NO.: 9], antisense GGCGGGTCATGGGAATAAC [SEQ ID NO.: 10], AQP-2 sense CCACCTCCTTGGGATCCATT [SEQ ID NO.:11], antisense GTGACGACAGCTGGAGCCA [SEQ ID NO.:12], AQP-3 sense CCCATCGTGTCCCCACTC [SEQ ID NO.:13], antisense GCCGATCATCAGCTGGTACA [SEQ ID NO.:14], AQP-4 sense ACATGGAGGTGGAGGACAACA [SEQ ID NO.:15], antisense CCCGGTCAACGTCAATCAC [SEQ ID NO.:16], Megalin sense GGCCTCAGTGTTGTGTATTA [SEQ ID NO.:17], antisense GAGCCAAGGGTTCACTAC [SEQ ID NO.:18]. All primers are given in the 5' to 3' direction. The PCR products were resolved on agarose gel and visualized using ethidium bromide.

Immunohistochemistry: The cells were fixed in ice-cold ethanol for 10 min. After 3 rinses with PBS, the samples were incubated with blocking solution containing PBS, 10% of FCS and 1% of bovine serum albumin (BSA) for 30 min. The antibodies against AQP-1, β-catenin, Oct3/4 (all from Sigma, USA), Ms X Hu Nuclei (HNuc, Chemicon International, USA) and cytokeratin-18 (CK-18, Zymed Technologies, USA) were diluted at a ratio of 1:100 and incubated for 2 h at room temperature. After 3 washes, the specimens were incubated for 45 min with appropriate secondary antibodies at a dilution of 1:200 in PBS containing 1% of BSA. DAPI was obtained from Sigma-Aldrich (Germany) for nuclear staining. The specimens were then analyzed using an IX71 Olympus microscope. Images were taken with a digital camera and processed using Photoshop 5.5 (Adobe Systems, San Jose, Calif., USA); a cell count was performed visually. The percentage of AQP-1-positive cells was obtained from the ratio of AQP-1-positive/DAPI-positive cells to AQP-1-negative/DAPI-positive cells.

Western Blotting: The cells were lysed in SDS-Laemmli buffer and sonicated. 15 µg of the total protein was loaded onto each lane and were separated according to their molecular weight in SDS-PAGE. The proteins were transferred to polyvinylidine fluoride (PVDF) membrane (Millipore, Bedford, USA) using the semi-dry Western blot apparatus (BIO-RAD, USA) at 15 V for 30 min. The remaining binding sites were blocked with PBS containing 5% of non-fat dry milk and 0.02% of Tween for 1 h at room temperature. The membrane was incubated with either AQP-1, β-catenin, Oct3/4, GAPDH (all from Santa Cruz Biotechnology, USA) and cytokeratin-18 (CK-18, Zymed Technologies, USA) overnight at 4° C. After 3 washing steps, the membrane was incubated with alkaline phosphate-conjugated secondary antibodies (Dianova, Germany) for 45 min. The blot was developed with a BCIP/NBT Kit (Zymed Technologies, USA). The immunoblots were documented using a Scan Jet 6200 C scanner (Hewlett Packard, Greely, USA). The assessment of the apparent molecular weight was done by means of SDS-PAGE standards, which were run in parallel in each experiment (n=6).

Flow Cytometry: 1 million cells were suspended in 80 µl of PBS containing 0.5% of BSA and 2 mM of ethylenediaminetetraacetic acid (EDTA). 20 µl of FcR blocking reagent were added. Subsequently, 10 µl of the phycoerythrin (PE)-conjugated antibodies CD31, CD45, CD56, CD133 and CD326 (all obtained from Miltenyi Biotec, Germany) were added for 10 min. Control experiments were performed without antibody administration and isotype controls. The cells were washed three times with buffer addition and centrifugation for 10 min at 300×g. The analysis was performed using a LSR II 3-laser FAQS analyzer (BD Biosciences, USA).

Water Transport Assay Using Calcein: Cells were cultured in a monolayer in tissue culture plates for at least 24 h prior to the assay. The cells were washed with PBS (without calcium and magnesium salts) three times, each for 1 min. The cells were loaded with calcein-AM (Invitrogen, USA) at a final concentration of 1.6 µM in PBS for 10 min, followed by 3 washing steps with PBS, each for 1 min. Cells were then live imaged in a fluorescent microscope setup with a CCD camera. The medium was changed to a hypotonic (0.06% NaCl in water) solution. Time lapse images were taken at an interval of 10 s for 10 min. The Metamorph software (Molecular Devices, USA) was used to measure the fluorescence intensity.

Bioreactor Set-Up and In Vivo Experiments: A SUPOR-800 polysulfone membrane (Pall Corporation, USA) with a pore size of 0.8 µm was coated for 1 h with MATRIGEL™ diluted 1:20 in REGM. Subsequently, differentiated hES cells were seeded onto the membrane, and cultured in REGM for 24 h under 5% of $CO_2$ at 37° C. The membrane with the cells was then placed in a bioreactor that has an inlet and an outlet. REGM was superfused over the membrane with the adherent hES cells at a flow rate of 0.1 ml/min, with recirculation of the culture medium through gas-permeable silicone tubes. The system was maintained under 5% of $CO_2$ at 37° C., with the silicone tubes allowing for gas exchange (27). The membrane with the cells was subjected to further analysis after 7-10 days of perfusion culture.

The animal experiments were conducted according to the approved IACUC application #060160 and NUS-IRB Reference Code 06-052. SCID mice were anesthetized and 1 million cells were injected under the renal capsule. After 6 weeks, the kidneys were removed and paraffin-embedded. 6-µm sections were cut using a microtome, and stained with Hematoxylin & Eosin.

Results

The HUES-7 cell line obtained from the Howard Hughes Medical Institute (USA) were maintained in an embryonic status on a mouse embryonic fibroblast (MEF) feeder layer (FIG. 1a) (16). The hES cells were subcultured twice on a surface coated with MATRIGEL™ diluted in Knock-out Dulbecco's modified Eagle's medium (DMEM) using conditioned medium collected from the MEF feeder layer (FIGS. 1a and b) to obtain fibroblast-free culture conditions (17-19). Expression of Oct3/4 (FIG. 1b), Sox2, CD9 and Nanog (FIG. 1c) confirmed the undifferentiated status under both conditions.

To initiate differentiation, the cells were cultured in a renal epithelial growth medium (REGM) for 10 days. The REGM comprises a renal epithelial basal medium (REBM) supplemented with several factors, such as 0.25% of fetal calf serum (FCS), epidermal growth factor (EGF), insulin, hydrocortisone, epinephrine and T3, each at 0.1% of concentration. To mimic the epithelial basement membrane, various culture surfaces with different ECM components such as fibronectin, laminin, collagen type IV and MATRIGEL™ were examined.

Figure 2:
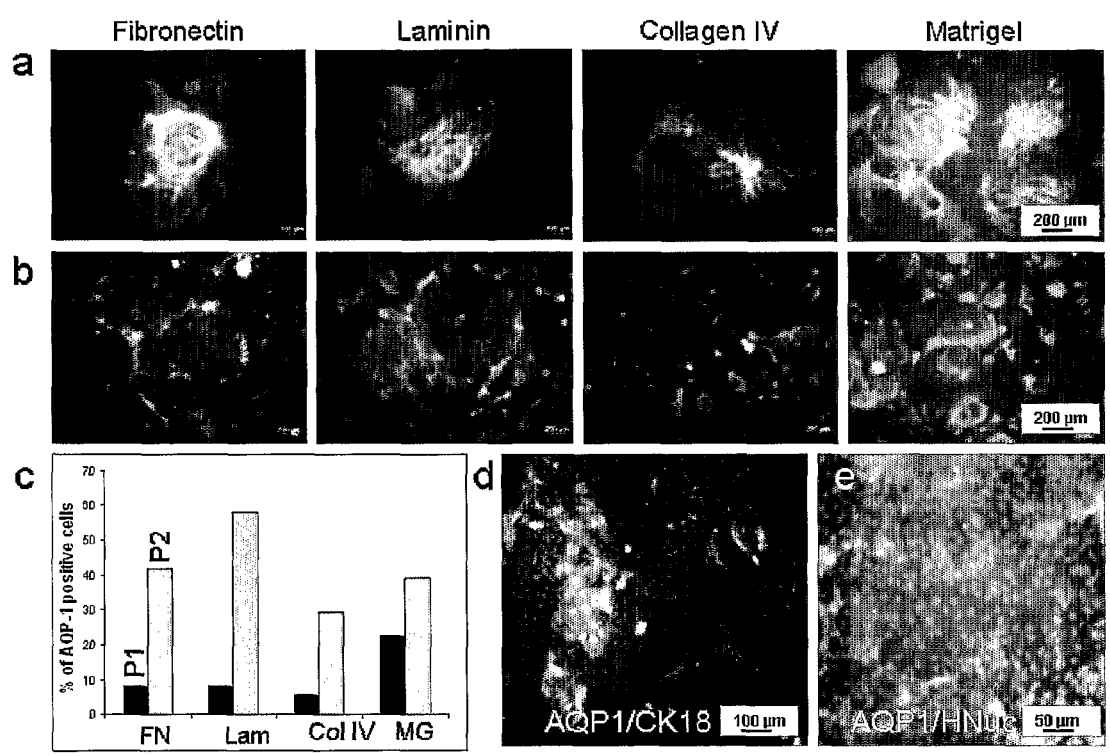
FIG. 2: Differentiation of hES Cells into AQP-1 Expressing Epithelial Cells. a, hES cells cultured on fibronectin (FN), laminin (Lam), collagen type IV (Col IV) and MATRIGEL™ (MG) for 10 days were immunostained with AQP-1 (red) and cytokeratin-18 (green). DAPI was used to stain the nucleus (blue). b, hES cells subcultured under the same culture conditions were immunostained with AQP-1 (red) along with DAPI (blue). a-c, Increased AQP-1 expression could be found when cells were cultured on MATRIGEL™, and when cells were subcultured on all four selected ECM molecules. d, Double staining experiments showed that differentiated hES cells expressing AQP-1 (red) were epithelial cells stained with cytokeratin-18 (green). e, Differentiated hES cells, in particular the AQP-1 expressing cells (green), were stained positive for HNuc (red), indicating their human origin.
Figure 3:
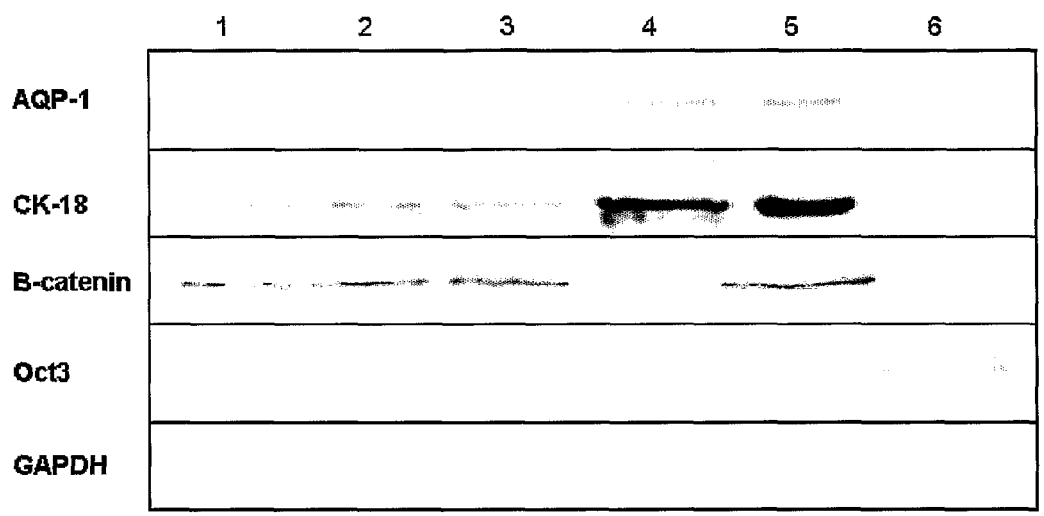
FIG. 3: Protein Profile of Undifferentiated (lane 6) and Differentiated hES Cells (lanes 1-5). Total protein was extracted from cells grown on fibronectin (lane 1), laminin (lane 2), collagen IV (lane 3), MATRIGEL™ (lane 4), subcultured on fibronectin (lane 5), and undifferentiated hES cells (lane 6), and subjected to SDS-PAGE, followed by electrotransfer onto PVDF membranes. The membranes were probed with antibodies such as AQP-1, CK-18, β-catenin, Oct3/4 and GAPDH. Undifferentiated hES cells (lane 6) show no expression for AQP-1 and β-catenin, and a weak expression for cytokeratin-18, while expression of Oct3/4 was maintained. In contrast, under nephrogenic culture conditions, up-regulation of AQP-1, CK-18 and β-catenin was observed. This expression pattern was found at higher intensities when the cells were cultured on MATRIGEL™ (lane 4), and subcultured on fibronectin (lane 5). These results indicate the adoption of a functional epithelial phenotype (n=6).

Initial experiments with DMEM culture media containing 10% of FCS revealed only very few attached hES cells. However, REGM caused a significant cell attachment and cell spreading in all ECM coatings applied. After 10 days of culture in REGM, immunohistochemistry with AQP-1 antibody showed similar expression pattern (with 5-10% of positive cells) for fibronectin, laminin and collagen IV, while MATRIGEL™ yielded a higher positive expression of AQP-1 (with 22% of positive cells (FIG. 2a)). Subculture of the hES cells on the same ECM led to a further increase in the AQP-1 positive cells in all 4 ECM coatings (FIG. 2b). The percentage of AQP-1 expressing cells is summarized in FIG. 2c. The REGM culture medium significantly promoted cell spreading and AQP-1 expression in hES cells. In addition, the subculture of hES on the same ECM and culture in REGM led to an increased number of AQP-1 expressing cells, independent of the respective ECM type. Dual staining with CK-18 antibody revealed that all AQP-1 expressing cells express CK-18 (FIG. 2d), indicating their epithelial phenotype (28). At the same time, all AQP-1 positive cells were positive for the human nuclear factor (hNuc), indicating their human origin (FIG. 2d). To confirm the results obtained in immunohistochemistry, Western blot was performed with the same samples and antibodies used for immunohistochemistry (FIG. 3). Western blot verified an increased expression of AQP-1 in REGM after 10 days of culture on MATRIGEL™, and when the cells were subcultured on the same ECM coating. A parallel result was seen for CK-18 and β-catenin, two epithelial-associated proteins. No band or a very faint band was found for the undifferentiated hES cell population. In addition, under the differentiation conditions, the expression of stem cell specific markers Oct3/4 was reduced, correlating with the up-regulation of renal markers towards an epithelial phenotype.

Figure 4:
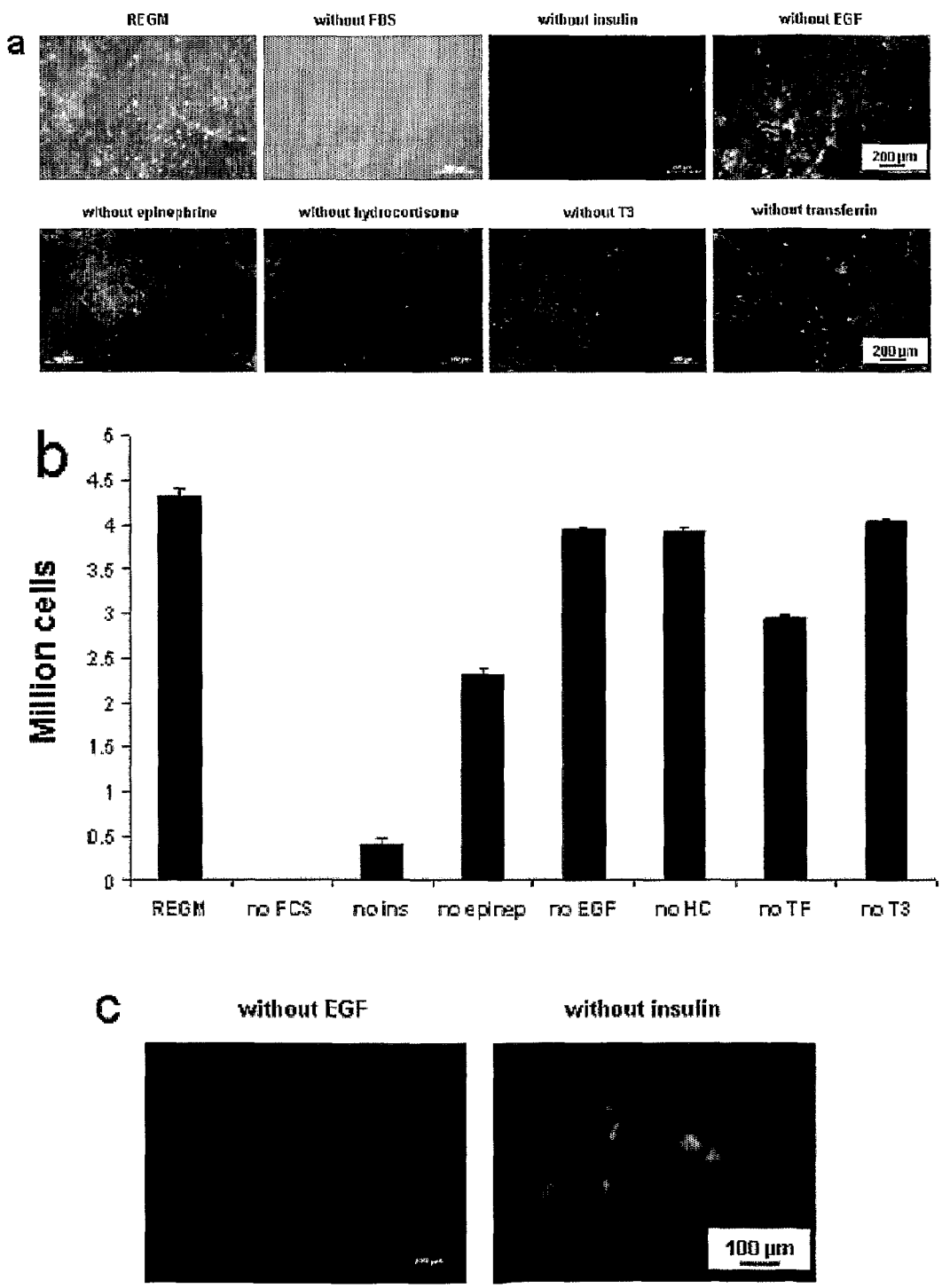
FIG. 4: Individual Component Analysis on hES Cell Attachment, Growth and Cell Proliferation. a, The effect of omitting single factors in REGM. Few cells were attached to the MATRIGEL™ surface in the absence of FBS. All other conditions led to cell attachment and growth. b, Role of various factors on cell proliferation. Insulin, epinephrine (epinep) and transferrin (TF) were shown to be important for hES cell proliferation. EGF, hydrocortisone (HC) and T3 had a minor effect on hES cell proliferation. c, Role of EGF and insulin on the AQP-1 expression. Fewer AQP-1 expressing cells were observed in REGM depleted with EGF, whereas AQP-1 expression was not significantly affected in the absence of insulin.

REGM is a complex culture medium containing various factors. To assess the influential factors affecting cell attachment and growth, factors were omitted one by one from the REGM (FIG. 4). After 10 days of culture, it was observed that fetal bovine serum (FBS) was essential for hES cell attachment even with MATRIGEL™ coating. In addition, these factors influenced the cell proliferation by different degrees. In particular, insulin showed a significant impact on cell proliferation. A reduction of over 90% in cell count was observed when insulin was not added to the media for cell growth. Reductions of ~45% and ~30% in cell counts were noted when epinephrine and transferrin were not supplemented in the media (FIGS. 4a and b). The role of various factors in the REGM culture medium on the AQP-1 expression was also investigated. AQP-1 expression was detected at different levels under the various culture conditions. When EGF was excluded, there were only a few cells that were AQP-1 positive, while many cells showed AQP-1 expression without insulin in the media (FIG. 4c).

Figure 5:
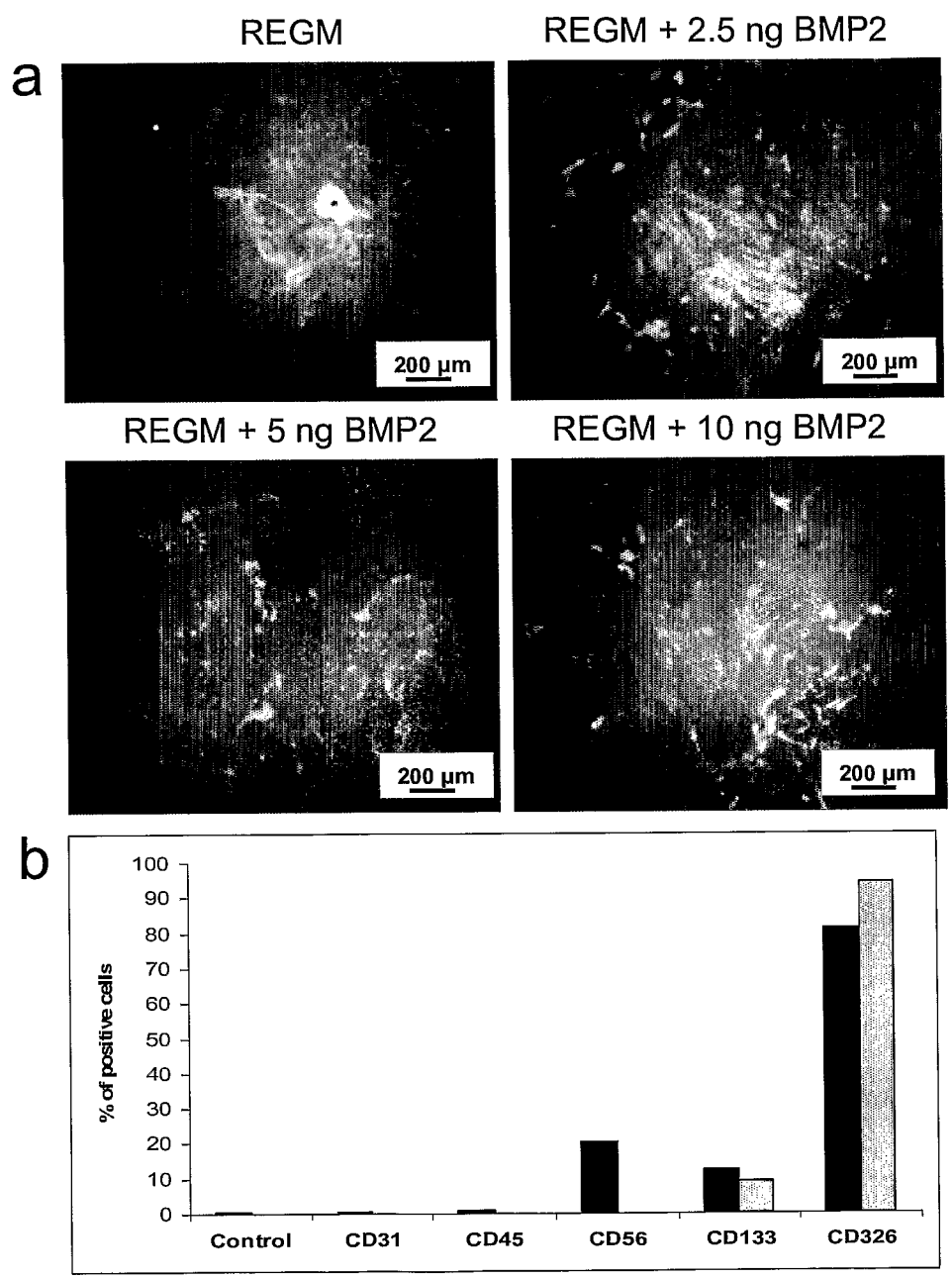
FIG. 5: Effect of BMP-2 on the AQP-1 and CD Receptor Expression in Differentiated hES Cells. a, REGM culture medium with BMP-2 caused an increased expression of AQP-1 in differentiated single cells compared to plain REGM, where a more clonal AQP-1 expression was observed. b, Differentiated hES cells (black bars) showed expressions of CD56, CD133 and CD326. CD133 and CD326 expressions were also observed with primary human proximal tubule cells (grey bars), indicating a similar phenotype as the differentiated hES cells with regard to their CD receptor expression profile.

It is known that during embryonic development, the kidney and derived tubular cells arise from the mesodermal germ layer beside cardiac, skeletal and smooth muscle cells (29-31). It has been shown that BMP-2 acts as a morphogenetic factor for mesodermal specification, and this is also underscored by the fact that BMP-2 can direct embryonic stem cells into a heart muscle cell type (31). Hence, it was examined whether BMP-2 has any effect on the hES cells differentiation into AQP-1 positive cells (FIG. 5a). Upon treatment with BMP-2 (in the range of 2.5 to 10 ng/ml), an increased number of AQP-1 positive cells was observed. A more clonal expansion pattern was found when the cells were differentiated without BMP-2, whereas BMP-2 induced a more scattered expression pattern, indicating that AQP-1 expression could be caused by clonal expansion of AQP-1 expressing cells and by switching on the AQP-1 expression in single cells.

To assess further similarities of primary human proximal tubule cells and REGM differentiated hES cells, the CD receptor expression of both cell types (differentiated on MATRIGEL™ in REGM with no BMP-2 added) were analyzed using flow cytometry. It was found that human proximal tubulus cells expressed a high amount of CD326, which is typical for epithelial cells (32). In addition, a subpopulation of this cell type also expressed CD133. This is important since CD133 is expressed in a small population of human renal cortical cells, and it has been shown that these cells can regenerate into renal tubular structures and are classified as renal adult stem cells (33,34). A very similar distribution of CD326- and CD133-positive cells was observed for the hES cells, differentiated on MATRIGEL™ and with REGM, indicating that both cell types share a common expression profile (FIG. 5b). However, the present differentiation protocol induced expression of CD56-positive cells, which is normally expressed by neuronal cells (35), indicating the presence of a pool of differentiated cells.

Figure 6:
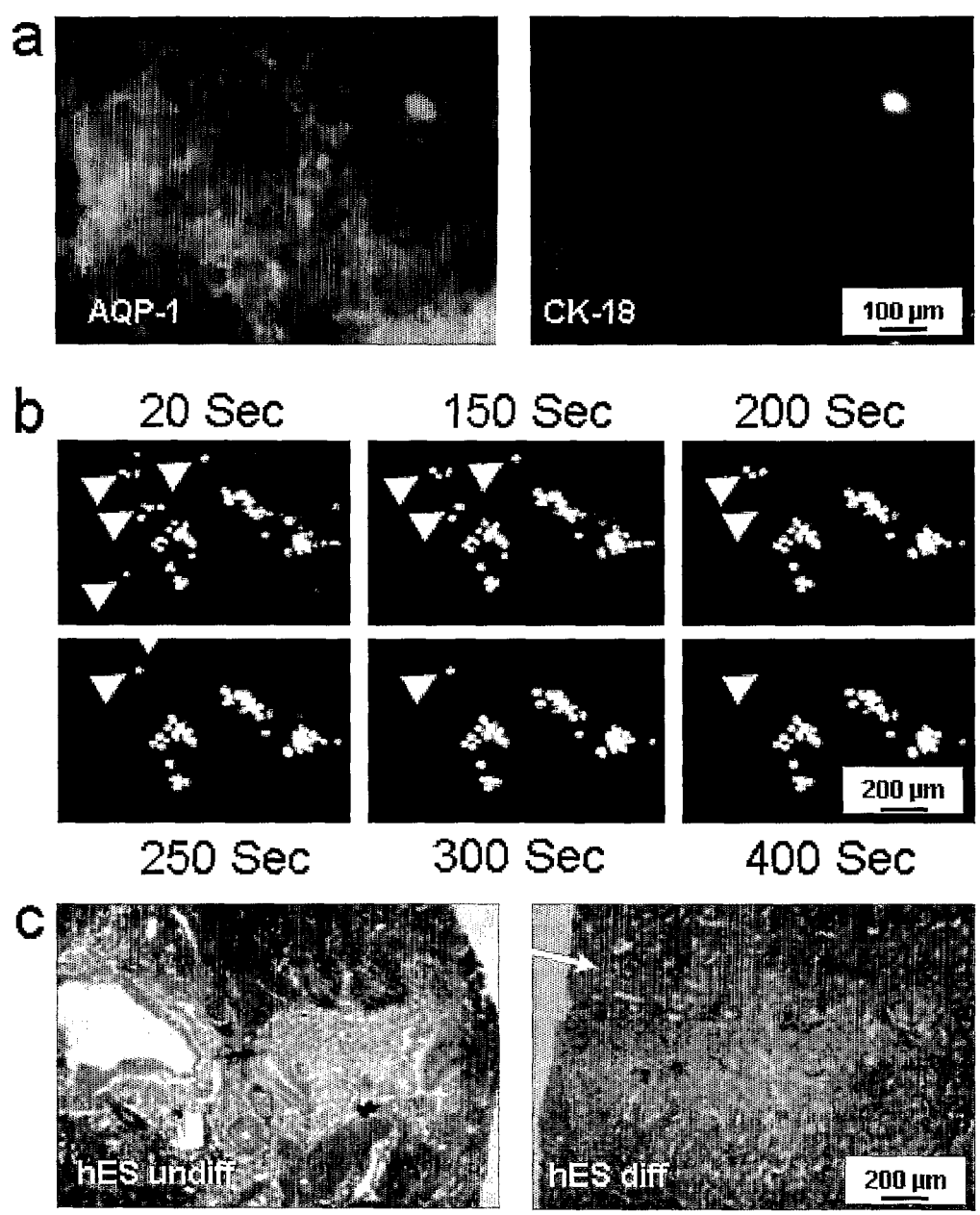
FIG. 6: In Vitro and In Vivo Function Assessments of Differentiated hES Cells. a, The differentiated cells were seeded onto a SUPOR-800 polysulfone membrane, and cultured in a perfusion bioreactor for 7-10 days. After perfusion culture, over 90% of the differentiated hES cells revealed simultaneous AQP-1 (red) and cytokeratin-18 (green) expressions (n=8). b, Water transport assay with calcein-loaded cells showed that several differentiated hES cells (marked with arrows) lost their calcein staining after exposure to a hypotonic solution, indicating the functionality of AQP-1 expressing channels. c, Injection of undifferentiated hES cells under the renal capsule of SCID mice led to teratoma tumor formation, whereas the injection of differentiated cells showed no tumor formation (the injection area was indicated by arrow).

To determine whether these cells display functional properties similar to proximal tubule, various in vitro and in vivo experiments were conducted in addition to examination of specific protein profile (FIG. 6). In a first set of experiments, the undifferentiated hES cells were seeded on a MATRIGEL™-coated polymeric porous membrane, which was placed into a perfusion bioreactor and superfused with REGM culture medium at a flow rate of 0.1 ml/min with recirculation of the culture medium (27). After 7 days, the membrane with the hES cells was investigated immunohistochemically for the phenotype expression. A confluent monolayer of cells covered the porous membrane entirely, and double immunostaining showed that more than 90% of the cells were positive for simultaneous expression of cytokeratin-18 and AQP-1 (FIG. 6a). These results showed that the cells could survive the perfusion culture condition with a high degree of AQP-1 expression, indicating their potential use in a bioartificial kidney application (BTAD). To determine the functionality of the AQP-1 expressing cells with regard to their water transport, the cells were first loaded with calcein in isotonic solution (300 mosM) and then exposed to a hypotonic solution (30 mosM) (8). The calcein in the differentiated cells was washed out by the hypotonic solution, whereas other cells retained their calcein staining, indicating that a portion of the cells exhibited functional water transport (FIG. 6b). In addition, undifferentiated hES cells and differentiated cells were injected under the renal capsule of SCID mice. After 6 weeks, the histological examination revealed teratoma formation in the mice injected with undifferentiated cells, while those with the differentiated cells exhibited no tumor formation (FIG. 6c). In the latter case, the injection area was characterized by dilated tubules, indicating dysplastic changes, which are likely to be induced by the injection procedure (also found in control experiments where the needle was inserted without cell injection (data not shown).

Figure 7:
FIG. 7: Expression of Megalin. This figure is a photograph of cells with fluorescent staining depicting expression of megalin.
Figure 8:
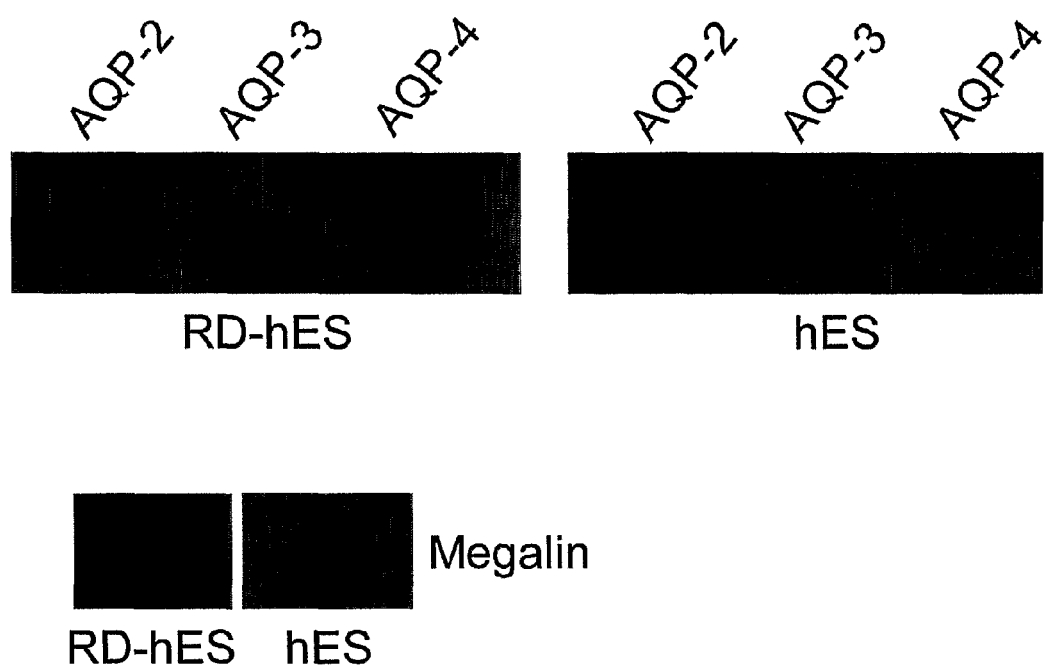
FIG. 8: Expression of AQP-2, AQP-3, AQP-4 and Megalin. PCR results for AQP-2, AQP-3, AQP-4 and megalin, showing expression in renal epithelial-like (RD-hES) cells differentiated according to the present method as compared to hES cells.

Expression of other cellular markers were compared. FIG. 7 shows fluorescent staining of Megalin in differentiated cells. FIG. 8 shows PCR products for AQP-2, AQP-3 and AQP-4 for differentiated (RD-hES) and undifferentiated (hES) cells.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Concentrations given in this specification, when given in terms of percentages, include weight/weight (w/w), weight/volume (w/v) and volume/volume (v/v) percentages.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. Itskovitz-Eldor J, Schuldiner M, Karsenti D, Eden A, Yanuka O, Amit M, Soreq H, Benvenisty N. Differentiation of human embryonic stem cells into embryoid bodies compromising the three embryonic germ layers. *Mol Med* 6 (2), 88-95 (200).

2. Little, M. H. Regrow or repair: Potential regenerative therapies for the kidney. *J Am Soc Nephrol* 17, 2390-2401 (2006).
3. Wang, G. et al. Noggin and bFGF cooperate to maintain the pluripotency of human embryonic stem cells in the absence of feeder layers. *Biochem Biophys Res Commun* 330, 934-942 (2005).
4. Bruce, S. J. et al. In vitro differentiation of murine embryonic stem cells toward a renal lineage. *Differentiation* 75 (5), 337-49 (2007).
5. Dantzler, W. H. Regulation of renal proximal and distal tubule transport: Sodium, chloride and organic anions. *Comp Biochem Physiol A Mol Integr Physiol* 136, 453-478 (2003).
6. Kriz, W., Kretzler, M., Provoost, A. P. & Shirato, I. Stability and leakiness: Opposing challenges to the glomerulus. *Kidney Int* 49, 1570-1574 (1996).
7. Murer, H., Hernando, N., Forster, I. & Biber, J. Proximal tubular phosphate reabsorption: Molecular mechanisms. *Physiol Rev* 80, 1373-1409 (2000).
8. Katsura, T. et al. Constitutive and regulated membrane expression of aquaporin 1 and aquaporin 2 water channels in stably transfected LLC-PK1 epithelial cells. *Proc Natl Acad Sci USA* 92, 7212-7216 (1995).
9. Nielsen, S., Kwon, T. H., Frokiaer, J. & Agre, P. Regulation and dysregulation of aquaporins in water balance disorders. *J Intern Med* 261, 53-64 (2007).
10. Verkman, A. S. Roles of aquaporins in kidney revealed by transgenic mice. *Semin Nephrol* 26, 200-208 (2006).
11. Humes, H. D. et al. Initial clinical results of the bioartificial kidney containing human cells in ICU patients with acute renal failure. *Kidney Int* 66, 1578-1588 (2004).
12. Saito, A. et al. Present status and perspectives of bioartificial kidneys. *J Artif Organs* 9, 130-135 (2006).
13. Reubinoff B E, Pera M F, Fong C Y, Trounson A, Bongso A. Embryonic stem cell lines from human blastocysts: somatic differentiation in vitro. *Nat Biotechnol* 18 (4), 399-404 (2000).
14. Kouskoff V, Lacaud G, Schwantz S, Fehling H J, Keller G. Sequential development of hematopoietic and cardiac mesoderm during embryonic stem cell differentiation. *Proc Natl Acad Sci USA* 102 (37), 13170-5 (2005).
15. Schuldiner M, Yanuka O, Itskovitz-Eldor J, Melton D A, Benvenisty N. Effects of eight growth factors on the differentiation of cells derived from human embryonic stem cells. *Proc Natl Acad Sci USA* 97 (21), 11307-12 (2000).
16. Singla D K, Sobel B E. Enhancement by growth factors of cardiac myocyte differentiation from embryonic stem cells: a promising foundation for cardiac regeneration. *Biochem Biophys Res Commun* 335 (3), 637-42 (2005).
17. Kim, D. & Dressler, G. R. Nephrogenic factors promote differentiation of mouse embryonic stem cells into renal epithelia. *J Am Soc Nephrol* 16, 3527-3534 (2005).
18. Richards, M., Fong, C. Y., Chan, W. K., Wong, P. C. & Bongso, A. Human feeders support prolonged undifferentiated growth of human inner cell masses and embryonic stem cells. *Nat Biotechnol* 20, 933-936 (2002).
19. Thomson, J. A. et al. Embryonic stem cell lines derived from human blastocysts. *Science* 282, 1145-1147 (1998).
20. Karp J M, Ferreira L S, Khademhosseini A, Kwon A H, Yeh J, Langer R S. Cultivation of human embryonic stem cells without the embryoid body step enhances osteogenesis in vitro. *Stem Cells* 24 (4), 835-43 (2006).
21. Xu, C. et al. Feeder-free growth of undifferentiated human embryonic stem cells. *Nat Biotechnol* 19, 971-974 (2001).
22. Mukhina, S. et al. Autocrine growth hormone prevents lactogenic differentiation of mouse mammary epithelial cells. *Endocrinology* 147, 1819-1829 (2006).
23. Tiranathanagul, K., Brodie, J. & Humes, H. D. Bioartificial kidney in the treatment of acute renal failure associated with sepsis. *Nephrology (Carlton)* 11, 285-291 (2006).
24. Atala, A. & Koh, C. J. Tissue engineering applications of therapeutic cloning. *Annu Rev Biomed Eng* 6, 27-40 (2004).
25. Yamamoto, M. et al. Branching ducts similar to mesonephric ducts or ureteric buds in teratomas originating from mouse embryonic stem cells. *Am J Physiol Renal Physiol* 290, F52-60 (2006).
26. Steenhard, B. M. et al. Integration of embryonic stem cells in metanephric kidney organ culture. *J Am Soc Nephrol* 16, 1623-1631 (2005).
27. Schumacher, K. et al. Perfusion Culture Improves the Maintenance of Cultured Liver Tissue Slices. *Tissue Eng* 13, 197-205 (2007).
28. Baer, P. C., Bereiter-Hahn, J., Schubert, R. & Geiger, H. Differentiation status of human renal proximal and distal tubular epithelial cells in vitro: Differential expression of characteristic markers. *Cells Tissues Organs* 184, 16-22 (2006).
29. Davies, J. A. Morphogenesis of the metanephric kidney. *ScientificWorldJournal* 2, 1937-1950 (2002).
30. James, R. G. & Schultheiss, T. M. BMP signaling promotes intermediate mesoderm gene expression in a dose-dependent, cell-autonomous and translation-dependent manner. *Dev Biol* 288, 113-125 (2005).
31. Pal, R. & Khanna, A. Similar pattern in cardiac differentiation of human embryonic stem cell lines, BG01V and ReliCellhES1, under low serum concentration supplemented with bone morphogenetic protein-2. *Differentiation* 75, 112-122 (2007).
32. Baeuerle, P. A. & Gires, O. EpCAM (CD326) finding its role in cancer. *Br J Cancer* 96, 417-423 (2007).
33. Bussolati, B. et al. Isolation of renal progenitor cells from adult human kidney. *Am J Pathol* 166, 545-555 (2005).
34. Sagrinati, C. et al. Isolation and characterization of multipotent progenitor cells from the Bowman's capsule of adult human kidneys. *J Am Soc Nephrol* 17, 2443-2456 (2006).
35. Maness, P. F. & Schachner, M. Neural recognition molecules of the immunoglobulin superfamily: Signaling transducers of axon guidance and neuronal migration. *Nat Neurosci* 10, 19-26 (2007).

What is claimed is:

1. A method of differentiating a human embryonic stem (hES) cell into a cell expressing AQP-1, CD-326 and CD-133, the method comprising:

culturing an undifferentiated hES cell in a renal epithelial medium that comprises (i) serum and (ii) an epithelial growth factor in the presence of an extracellular matrix (ECM) molecule, under conditions sufficient to induce differentiation of the hES cell to a cell expressing AQP-1, CD-326 and CD-133.

2. The method according to claim 1 wherein the renal epithelial medium comprises renal epithelial basal medium or renal epithelial growth medium.

3. The method according to claim 1 wherein the ECM molecule comprises at least one of fibronectin, laminin, collagen IV and Matrigel matrix.

4. The method according to claim 1 wherein the renal epithelial medium comprises renal epithelial growth medium and the epithelial growth factor and the serum are components of the renal epithelial growth medium.

5. The method according to claim 1 further comprising adding bone morphogenetic protein 2 to the renal epithelial medium before or during said culturing.

6. The method according to claim 1 further comprising adding bone morphogenetic protein 2 to the renal epithelial medium at a concentration of from about 2.5 to about 10 ng/ml before or during said culturing, wherein said culturing comprises growing the cell for 7-10 days, the renal epithelial medium comprises renal epithelial growth medium and the ECM molecule comprises Matrigel matrix, and wherein once differentiated, the cell expresses AQP-1, CD-326 and CD-133 and at least one of CK-18 and β-catenin.

* * * * *